(12) United States Patent
Schmidt (10) Patent No.: US 10,155,925 B2
(45) Date of Patent: Dec. 18, 2018

(54) ROTATING DUAL DOUBLE HELIX CONDUCTORS

(71) Applicant: Medical Energetics Ltd., Galway (IE)

(72) Inventor: David G. Schmidt, Poway, CA (US)

(73) Assignee: MEDICAL ENERGETICS LTD., Galway (IE)

(*) Notice: Subject to any disclaimer, the term of this patent is extended or adjusted under 35 U.S.C. 154(b) by 176 days.

(21) Appl. No.: 15/253,678

(22) Filed: Aug. 31, 2016

(65) Prior Publication Data
US 2017/0058251 A1    Mar. 2, 2017

Related U.S. Application Data (60) Provisional application No. 62/283,464, filed on Sep. 1, 2015.

(51) Int. Cl.
| | |
|---|---|
| *A61N 2/02* | (2006.01) |
| *C12M 1/42* | (2006.01) |
| *H01F 27/28* | (2006.01) |
| *C12N 13/00* | (2006.01) |
| *H01F 5/00* | (2006.01) |
| *H01F 7/20* | (2006.01) |
| *A01G 7/04* | (2006.01) |

(52) U.S. Cl.
CPC .............. *C12M 35/06* (2013.01); *A61N 2/02* (2013.01); *C12N 13/00* (2013.01); *H01F 5/00* (2013.01); *H01F 7/20* (2013.01); *H01F 27/28* (2013.01); *A01G 7/04* (2013.01)

(58) Field of Classification Search
CPC .............. A01G 7/04; A61N 2/02; H01F 27/28
See application file for complete search history.

(56) References Cited

U.S. PATENT DOCUMENTS

| | | |
|---|---|---|
| 1,898,661 A | 2/1933 | Hagen |
| 2,035,274 A | 3/1936 | Mougey |
| 2,297,454 A | 9/1942 | Berger |
| 2,850,666 A | 9/1958 | Brewer |
| 3,037,175 A | 5/1962 | Ruthroff |
| 3,066,295 A | 11/1962 | Krause |
| 3,519,964 A | 7/1970 | Chorney |
| 3,588,689 A | 6/1971 | Crawford |
| 3,683,393 A | 8/1972 | Self |
| 3,760,812 A | 9/1973 | Timm |
| 3,774,452 A | 11/1973 | Tullos |
| 4,131,759 A | 12/1978 | Felkel |
| 4,229,676 A | 10/1980 | Manoly |
| 4,266,532 A | 5/1981 | Ryaby |
| 4,439,702 A | 3/1984 | Belikov |
| 4,489,276 A | 12/1984 | Yu |
| 4,832,051 A | 5/1989 | Jarvik |
| 4,989,617 A | 2/1991 | Memberg |

(Continued)

FOREIGN PATENT DOCUMENTS

| | | |
|---|---|---|
| GB | 479841 A | 2/1938 |
| GB | 2480610 A | 11/2011 |

(Continued)

*Primary Examiner* — Christine H Matthews
(74) *Attorney, Agent, or Firm* — ARC IP Law, PC; Joseph J. Mayo (57) ABSTRACT

A system including one or more rotatable bodies having an underlying structure resembling a double helix may be arranged and used, to produce useful electromagnetic effects for various applications.

20 Claims, 8 Drawing Sheets

(56) References Cited

U.S. PATENT DOCUMENTS

| | | |
|---|---|---|
| 5,077,934 A | 1/1992 | Liboff |
| 5,079,458 A | 1/1992 | Schuster |
| 5,173,669 A | 12/1992 | Manoly |
| 5,182,537 A | 1/1993 | Thuis |
| 5,339,061 A | 8/1994 | Reick |
| 5,359,340 A | 10/1994 | Yokota |
| 5,366,493 A | 11/1994 | Scheiner |
| 5,464,456 A | 11/1995 | Kertz |
| 5,654,723 A | 8/1997 | Craven |
| 5,819,467 A | 10/1998 | Zucker |
| 5,851,206 A | 12/1998 | Guglielmi |
| 5,892,480 A | 4/1999 | Killen |
| 5,909,165 A | 6/1999 | Leupold |
| 5,954,630 A | 9/1999 | Masaki |
| 5,977,932 A | 11/1999 | Robinson |
| 6,005,462 A | 12/1999 | Myers |
| 6,169,523 B1 | 1/2001 | Ploussios |
| 6,239,760 B1 | 5/2001 | VanVoorhies |
| 6,300,920 B1 | 10/2001 | Pertl |
| 6,520,986 B2 | 2/2003 | Martin |
| 6,552,530 B1 | 4/2003 | Vaiser |
| 6,770,023 B2 | 8/2004 | Vaiser |
| 6,921,042 B1 | 7/2005 | Goodzeit |
| 6,978,179 B1 | 12/2005 | Flagg |
| 7,148,783 B2 | 12/2006 | Parsche |
| 7,154,368 B2 | 12/2006 | Sweeney |
| 7,375,449 B2 | 5/2008 | Butterfield |
| 8,323,328 B2 | 12/2012 | Martin |
| 8,463,407 B2 | 6/2013 | Bulkes |
| 8,652,023 B2 | 2/2014 | Schmidt |
| 8,653,925 B2 | 2/2014 | Schmidt |
| 8,749,333 B2 | 6/2014 | Schmidt |
| 8,919,035 B2 | 12/2014 | Schmidt |
| 8,961,384 B2 | 2/2015 | Schmidt |
| 9,030,283 B2 | 5/2015 | Schmidt |
| 9,370,667 B2 | 6/2016 | Schmidt |
| 9,406,421 B2 | 8/2016 | Schmidt |
| 9,504,845 B2 | 11/2016 | Schmidt |
| 2003/0011527 A1 | 1/2003 | Kokorin |
| 2003/0095022 A1 | 5/2003 | Boynton et al. |
| 2003/0158585 A1 | 8/2003 | Burnett |
| 2003/0169132 A1 | 9/2003 | Vaiser |
| 2003/0230427 A1 | 12/2003 | Gareis |
| 2005/0094989 A1 | 5/2005 | Halpin |
| 2005/0121396 A1 | 6/2005 | Kosakewich |
| 2005/0228209 A1* | 10/2005 | Schneider ......... A61B 5/04009 600/13 |
| 2007/0024520 A1 | 2/2007 | Preble |
| 2007/0258329 A1 | 11/2007 | Winey |
| 2008/0161884 A1 | 7/2008 | Chandler |
| 2008/0266203 A1 | 10/2008 | Rossetto |
| 2009/0083969 A1 | 4/2009 | Meinke |
| 2009/0206974 A1 | 8/2009 | Meinke |
| 2009/0260849 A1 | 10/2009 | Cardas |
| 2010/0005711 A1 | 1/2010 | McNeff |
| 2010/0057655 A1 | 3/2010 | Jacobson |
| 2010/0113862 A1 | 5/2010 | Kotowich |
| 2010/0114280 A1 | 5/2010 | Hill |
| 2010/0121131 A1 | 5/2010 | Mathes |
| 2010/0152811 A1 | 6/2010 | Flaherty |
| 2010/0179630 A1 | 7/2010 | Williams |
| 2012/0101366 A1 | 4/2012 | Ruohonen |
| 2012/0143285 A1 | 6/2012 | Wang |
| 2012/0223800 A1 | 9/2012 | Schmidt |
| 2013/0192129 A1 | 8/2013 | Schmidt |
| 2013/0211181 A1 | 8/2013 | Schmidt |
| 2013/0274542 A1 | 10/2013 | Volo et al. |
| 2013/0285782 A1 | 10/2013 | Schmidt |
| 2014/0097925 A1 | 4/2014 | Schmidt |
| 2014/0100412 A1 | 4/2014 | Schmidt |
| 2014/0218149 A1 | 8/2014 | Schmidt |
| 2014/0371514 A1 | 12/2014 | Schmidt |
| 2015/0119630 A1 | 4/2015 | Schmidt |
| 2015/0119631 A1 | 4/2015 | Schmidt |
| 2015/0119632 A1 | 4/2015 | Schmidt |
| 2015/0157871 A1 | 6/2015 | Schmidt |
| 2015/0283393 A1 | 10/2015 | Schmidt |
| 2015/0283394 A1 | 10/2015 | Schmidt |
| 2016/0172088 A1 | 6/2016 | Schmidt |
| 2016/0172101 A1 | 6/2016 | Schmidt |
| 2016/0247614 A1 | 8/2016 | Schmidt |
| 2016/0247617 A1 | 8/2016 | Schmidt |
| 2016/0365186 A1 | 12/2016 | Schmidt |

FOREIGN PATENT DOCUMENTS

| | | |
|---|---|---|
| WO | 2012118971 A2 | 9/2012 |
| WO | 2013112810 A1 | 8/2013 |
| WO | 2013123009 A1 | 8/2013 |

* cited by examiner

ROTATING DUAL DOUBLE HELIX CONDUCTORS

FIELD OF THE INVENTION

The invention relates to rotatable bodies that include one or more helically wound runners around which conductive wires are wound, devices including such rotatable bodies, (electrical) systems including such rotatable bodies, and/or applications using such rotatable bodies. Applications may include agricultural applications, medical applications, therapeutic applications, communication applications, energy production, energy conversion, energy transformation, energy transfer, adenosine triphosphate (ATP) production, ATP transfer, ATP processing, material science, metallurgy, chemical processing, propulsion, and/or other applications.

A body with one or more runners may be referred to as a coil. Devices and systems may include one or more coils, e.g. in specific and predetermined arrangements. The invention further relates to the manufacture of such bodies, devices, and/or systems. The invention further relates to methods of operation of such devices and systems, and applications thereof. The invention further relates to such devices and/or systems configured to generate electromagnetic effects such as electromagnetic fields. The invention further relates to such devices and/or systems configured to promote growth in organisms and organic matter by using electromagnetic effects such as electromagnetic fields

BACKGROUND OF THE INVENTION

It is known that spirally wound electrical conductors may exhibit certain electromagnetic properties and/or electromagnetic effects. For example, it is known that an electromagnetic coil may act as an inductor and/or part of a transformer, and has many established useful applications in electrical circuits. One or more coils may be used to exploit an electromagnetic field and/or other electromagnetic effects that are created when, e.g., one or more active current sources are operatively coupled to the one or more coils.

SUMMARY

One aspect of the invention relates to a system comprising one or more rotatable bodies, one or more power sources, one or more conductive wires, and/or other components. Individual bodies may be rotatable with respect to a support structure. Individual bodies may include two or more intertwined helically wound runners. A first runner may be coupled to the second runner by struts and/or held in position through other support structures. Individual runners may have a helical shape. Individual bodies may be arranged in toroidal shapes. One or more conductive wires may be spirally wound around at least one runner.

Specific alternating currents may be supplied to the conductive wires. In some implementations, conductive wires for each individual body may be supplied with a high-frequency carrier wave that is modulated with an acoustic signal. In some implementations, the speed of the rotation, i.e. a number of revolutions per second, may match or correspond a frequency of a supplied alternating current. In some implementations, different acoustic signals may be used for different bodies in the system.

As used herein, the term "agriculture" refers to the cultivation of animals, plants, fungi, and other life forms for food, fiber, bio-fuel, medicinal products and other products used to sustain and/or enhance human life. This cultivation may be referred to as agricultural application. Other applications are envisioned within the scope of this disclosure. For example, applications may include regenerative medicine, stem cell culturing, wound healing, material science, metallurgy, chemical processing, propulsion, and/or other applications.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION

Figure 1:
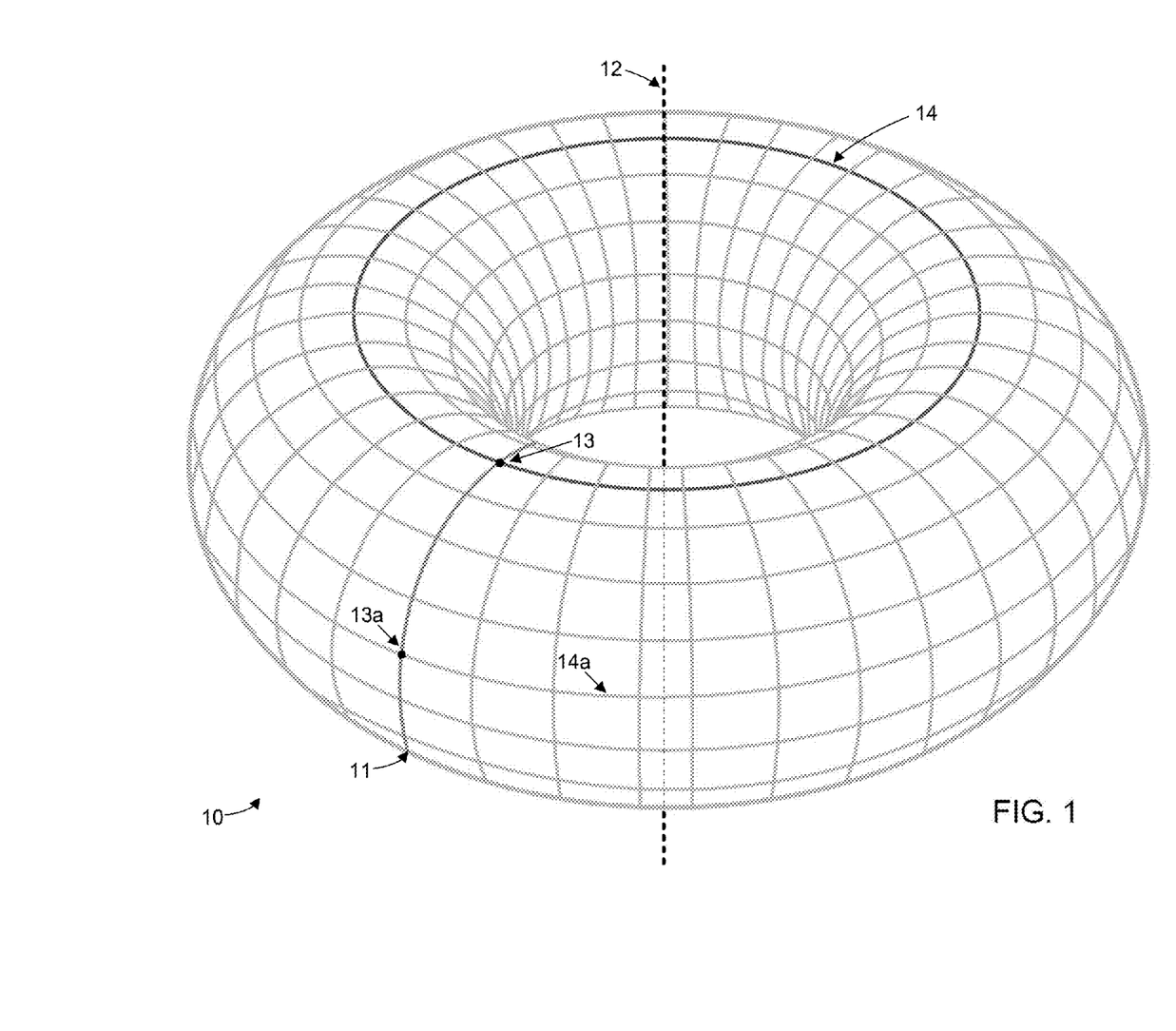
FIG. 1 illustrates a toroidal shape.

FIG. 1 illustrates a toroidal shape 10. A toroidal shape such as shape 10 may be formed by revolving a circle 11 (partially shown in FIG. 1) in three-dimensional space about an axis 12 that is coplanar with circle 11. Toroidal shape 10 may be informally referred to as a donut shape or a bagel shape. Axis 12 may be said to go through the donut hole of toroidal shape 10. The surface of toroidal shape 10 may be a torus. Circle 11 may include a point 13, a point 13a, and other points. As circle 11 is revolved to form toroidal shape 10, point 13 describes a circle 14 that defines a plane. This plane is perpendicular to axis 12. Different points on circle 11 describe different circles on the surface of toroidal shape 10. As circle 11 is revolved, point 13a describes a circle 14a that defines a plane. This plane bisects toroidal shape 10 and is perpendicular to axis 12. In some implementations, for a particular point 13a and a particular circle 14a, the defined plane bisects toroidal shape 10 into two similar, congruent, circular, and/or isometric halves, e.g. as if cutting a bagel in half such that the surface area of the cut has the shape of a mathematical ring or annulus (i.e. a first circle with a relatively smaller radius completely inside a second circle with a relatively larger radius, with both circles being concentric, the term "relatively" being used to relate the first circle and the second circle).

Figure 2:
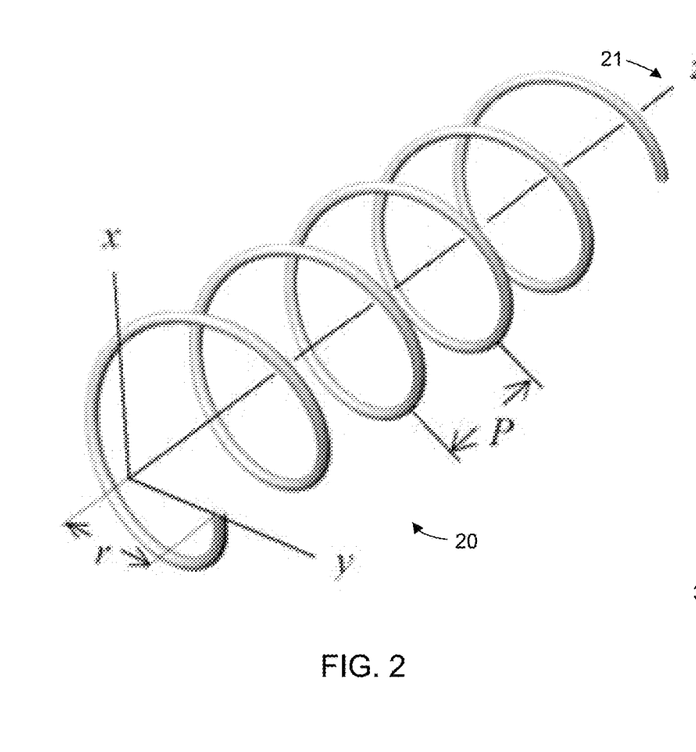
FIG. 2 illustrates a helical shape.

FIG. 2 illustrates a helical shape 20. A helical shape such as shape 20 may be formed by a curve in three-dimensional space that has the property that the tangent line at any point makes a constant angle with a fixed line called an axis 21 (labeled "z" in FIG. 2, and perpendicular to both the "x" and "y" axes in FIG. 2). The width of one complete helix turn or revolution, measured parallel to axis 21, is called pitch (labeled "P" in FIG. 2). The shortest distance from helical shape 20 to axis 21 is called the radius (labeled "r" in FIG. 2). Helical shape 20 may have a constant radius, and be referred to as a circular helix. Note that in some implementations, an axis similar to axis 21 may be curved instead of being straight, as depicted in FIG. 2.

Figure 3:
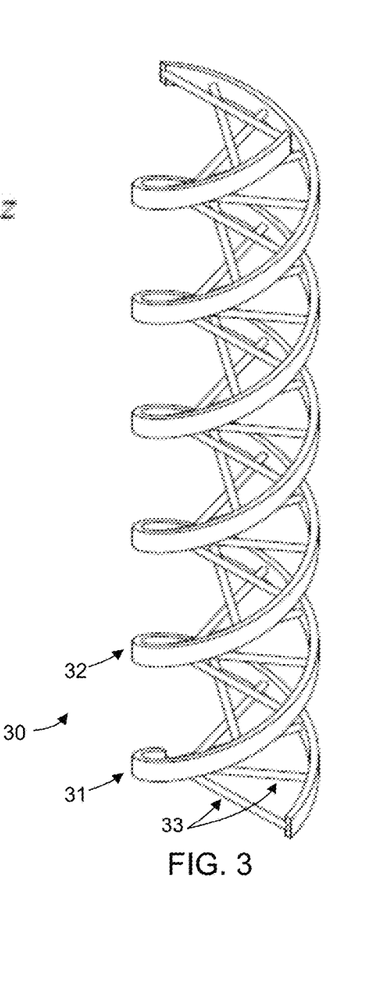
FIG. 3 illustrates an exemplary body including two intertwined helically wound runners in the shape of a double helix, the runners being coupled and/or supported by struts.

FIG. 3 illustrates an exemplary body 30 including two intertwined helically wound runners, a first runner 31 and a second runner 32, in the shape of a double helix, the runners being coupled and/or supported by struts 33. In some implementations, the runners of a double helix may be supported by other support structures. The double helix may include two helical shapes, each of which may be similar to helical shape 20 as shown in FIG. 2. It is noted that the shape of body 30 resembles the general shape of deoxyribonucleic acid (DNA), e.g. a double helix. A helical shape may have a straight axis, as shown in FIG. 2 and FIG. 3, or a curved axis as shown in, e.g., FIG. 4.

Figure 4:
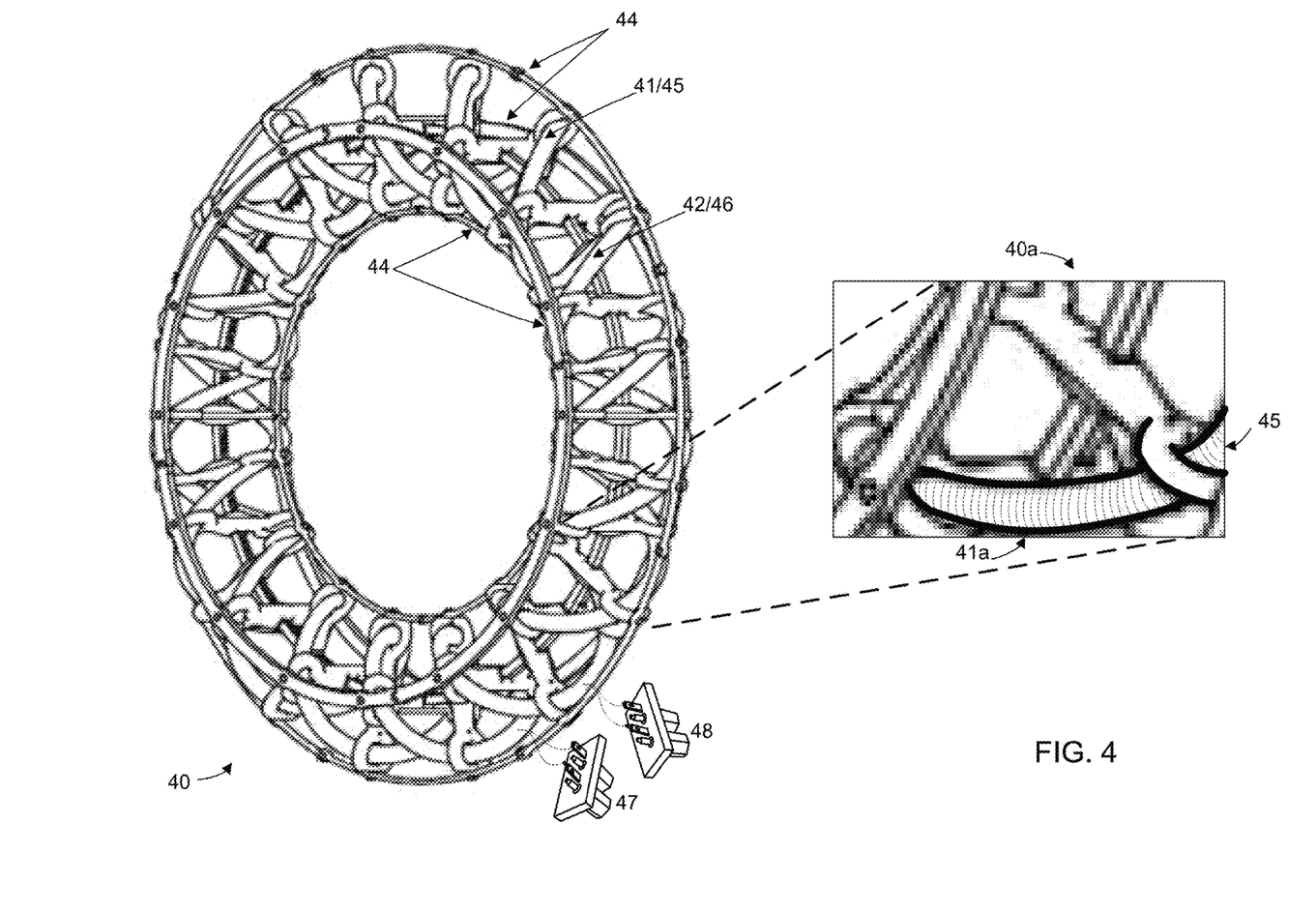
FIG. 4 illustrates an exemplary body including two intertwined helically wound runners, the body arranged to form a toroidal shape.

FIG. 4 illustrates an exemplary body 40 including two intertwined helically wound runners, a first runner 41 and a second runner 42, in the shape or form of a double helix, the body 40 being arranged to form a toroidal shape, the toroidal shape being similar to toroidal shape 10 as shown in FIG. 1. Referring to FIG. 4, body 40 may be arranged such that the axis of the double helix is not straight but curved, e.g. in a circle or oval. The runners of body 40 may be supported by support structures 44. As shown in a view 40a that illustrates a magnified section of body 40, which includes a section 41a of runner 41, a wire 45 may be wound around runner 41. In some implementations, wire 45 may be wound clockwise. In some implementations, wire 45 may be arranged and/or wound at a fixed distance of a particular runner, e.g. runner 41. In some implementations, wire 45 may be wound around runner 41 in multiple revolutions, wire 45 being arranged such that runner 41 and wire 45 are separated by a single and constant distance throughout individual ones of the multiple revolutions, the single and constant distance remaining unchanged throughout the individual ones of the multiple revolutions.

In some implementations, wire 45 may be wound counter-clockwise. Wire 45 may be conductive. Wire 45 may be too fine to be visible in a figure without magnification. A wire such as wire 45 may be insulated, uninsulated, or partially insulated and partially uninsulated, as may any wire listed in any figure included in this description. As used herein, a "wire" may include a set of twisted wires (which may interchangeably be referred to as a "twisted wire"), including but not limited to a set of two twisted wires. A wire 46 may be wound around runner 42 in a manner similar to wire 45 and runner 41. A connector 47 may be electrically coupled to twisted wire 45. For example, as shown in FIG. 4, both ends of twisted wire 45 may be electrically coupled to connector 47. A connector 48 may be electrically coupled to twisted wire 46. For example, as shown in FIG. 4, both ends of twisted wire 46 may be electrically coupled to connector 48. One or more power sources and/or current sources (not shown in FIG. 4) may be electrically coupled to connector 47 and/or connector 48 to supply current to twisted wire 45 and/or twisted wire 46, respectively, such that an electromagnetic effect (e.g. an electromagnetic field) is created around and/or near body 40.

In some implementations, a system may include one or more bodies that are similar to body 40. Such a system may be configured to generate and/or create an electromagnetic effect around and/or near the one or more bodies. By virtue of this electromagnetic effect, such a system may be used for agricultural applications, e.g. to promote growth of organisms, and/or be used for other applications. In some implementations, such a system may be used to improve and/or promote the health of organisms. As shown in FIG. 4, by way of non-limiting example, body 40 may be arranged such that body 40 is substantially vertical. For example, the plane that bisects the toroidal shape of body 40 into two similar, congruent, circular, and/or isometric halves (e.g. as described in relation to FIG. 1) may be arranged such that the plane is substantially vertical. In some implementations, the plane that bisects the toroidal shape of body 40 into two similar, congruent, circular, and/or isometric halves (e.g. as described in relation to FIG. 1) may be arranged such that the plane is substantially horizontal.

In some implementations, body 40 may be constructed such that its diameter is about 4 inches, about 6 inches, about 8 inches, about 10 inches, about 1 foot, about 18 inches, about 2 feet, about 30 inches, about 3 feet, about 4 feet, about 5 feet, about 6 feet, about 7 feet, about 8 feet, about 9 feet, about 10 feet, and/or other sizes. In some implementations, body 40 may have a diameter of about 20 inches. In some implementations, body 40 may have a diameter of about 50 or 60 inches.

Figure 5:
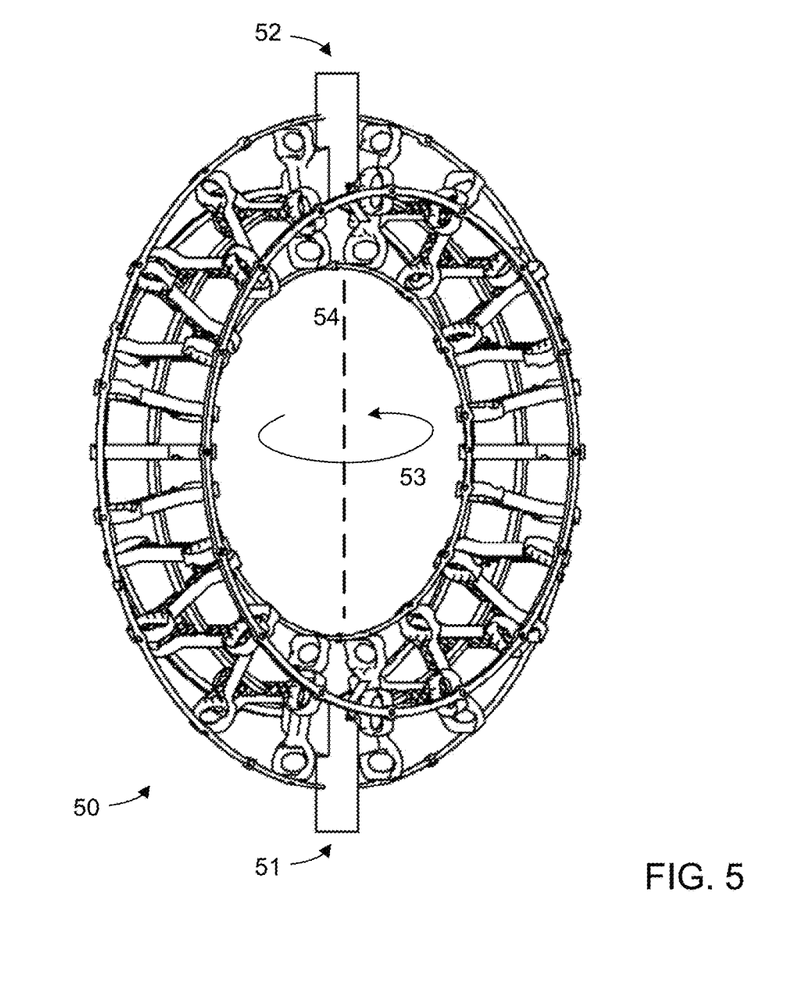
FIG. 5 illustrates an exemplary body that includes rotational components.

FIG. 5 illustrates an exemplary rotatable body 50 that is similar to body 40 in FIG. 4, except for the addition of rotational elements 51 and 52. Body 50 may include components of body 40 that are not depicted in FIG. 5, including but not limited to two intertwined helically wound runners in the shape of a double helix. Body 50 may include a rotational axis 54 through rotational elements 51 and 52. Rotatable body 50 may be rotatable around rotational axis 54, for example in a direction 53.

Figure 6A:
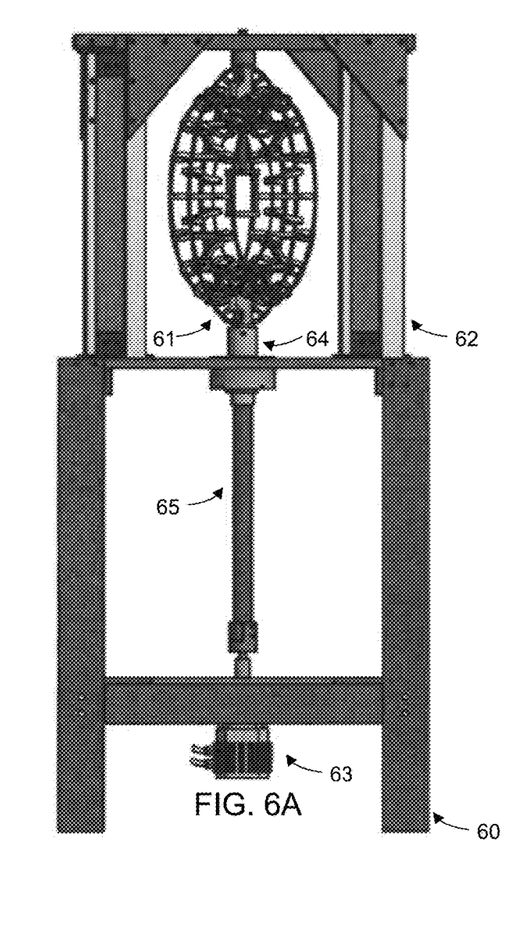
FIGS. 6A and 6B illustrate arrangements of systems that include a rotatable body.

FIG. 6A illustrates an arrangement of a system 60 that includes a rotatable body 61, a support structure 62, a power source 63, and/or other components. Body 61 may be similar to body 40 and/or body 50 of FIG. 4 and FIG. 5. Body 61 may include components of body 40 or body 50 that are not depicted in FIG. 6A, including but not limited to two intertwined helically wound runners in the shape of a double helix, conductive wires, connectors, and/or other components. Note that some components such as connectors and current sources (described elsewhere in this disclosure) are not depicted in FIG. 6A, but may be included in system 60. Support structure 62 may be configured to support body 61 in such a way that body 61 is rotatable with respect to support structure 62. Power source 63 may be configured to provide power to rotate body 61, e.g. via a driveshaft 65 and/or a slip ring (not shown), around a rotational axis. In some implementations, system 60 may include one or more rotational elements 64 that are similar or the same as rotational elements 51 and/or 52 in FIG. 5. Referring to FIG. 6A, power source 63 (and/or another power source such as, e.g., a current source) may further be configured to provide one or more alternating currents to body 61 (in particular, to a conductive wire wound around a helically wound runner of body 61).

Figure 6B:
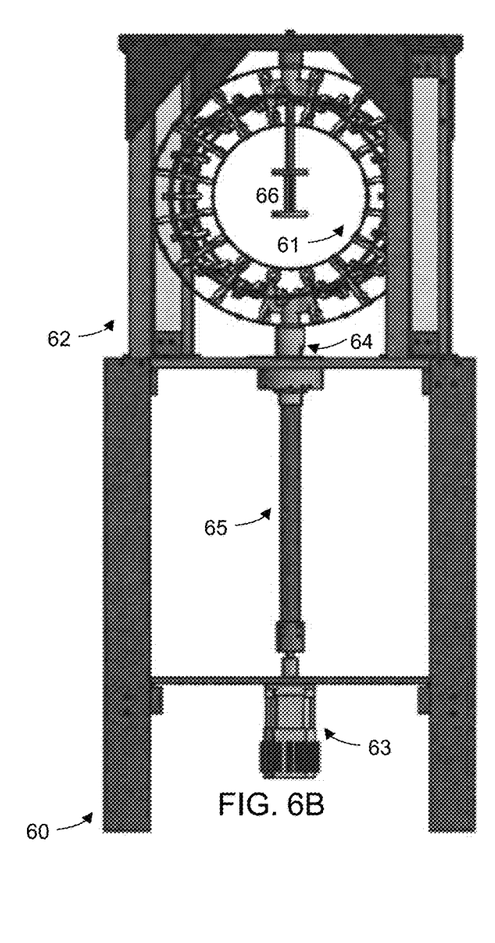

FIG. 6B illustrates an arrangement of system 60 similar to or the same as system 60 in FIG. 6A, depicted at a different viewing angle. The same components as described regarding FIG. 6A may be included in FIG. 6B. System 60 may include a stationary structure 66 in proximity of the center of body 61. In some implementations, the stationary structure 66 may be referred to as a treatment chamber. Stationary structure 66 may be configured to remain stationary during rotation of body 61. In some implementations, stationary structure 66 may be used to support, hold, and/or carry an organism. The organism may be any cultivated lifeform(s)—not just animals—used in agriculture applications, medical applications, and/or other applications. In some implementations, the organism may include chicken, cow, pig, lamb, goat, bird, fish, crustacean, mollusk, reptile, and/or other animals. In some implementations, the organism may include a sample, tissue, stem cells, living cells, and/or any other (organic) matter that may benefit from being subjected to an electromagnetic effect generated by system 60. In particular, tests have shown that the regeneration period for planarians (after having been cut in half) was reduced from 17 days to 3 days when placed in stationary structure 66. The depiction and number of organisms in FIG. 6A/6B is not intended to be limiting in any way.

Figure 7:
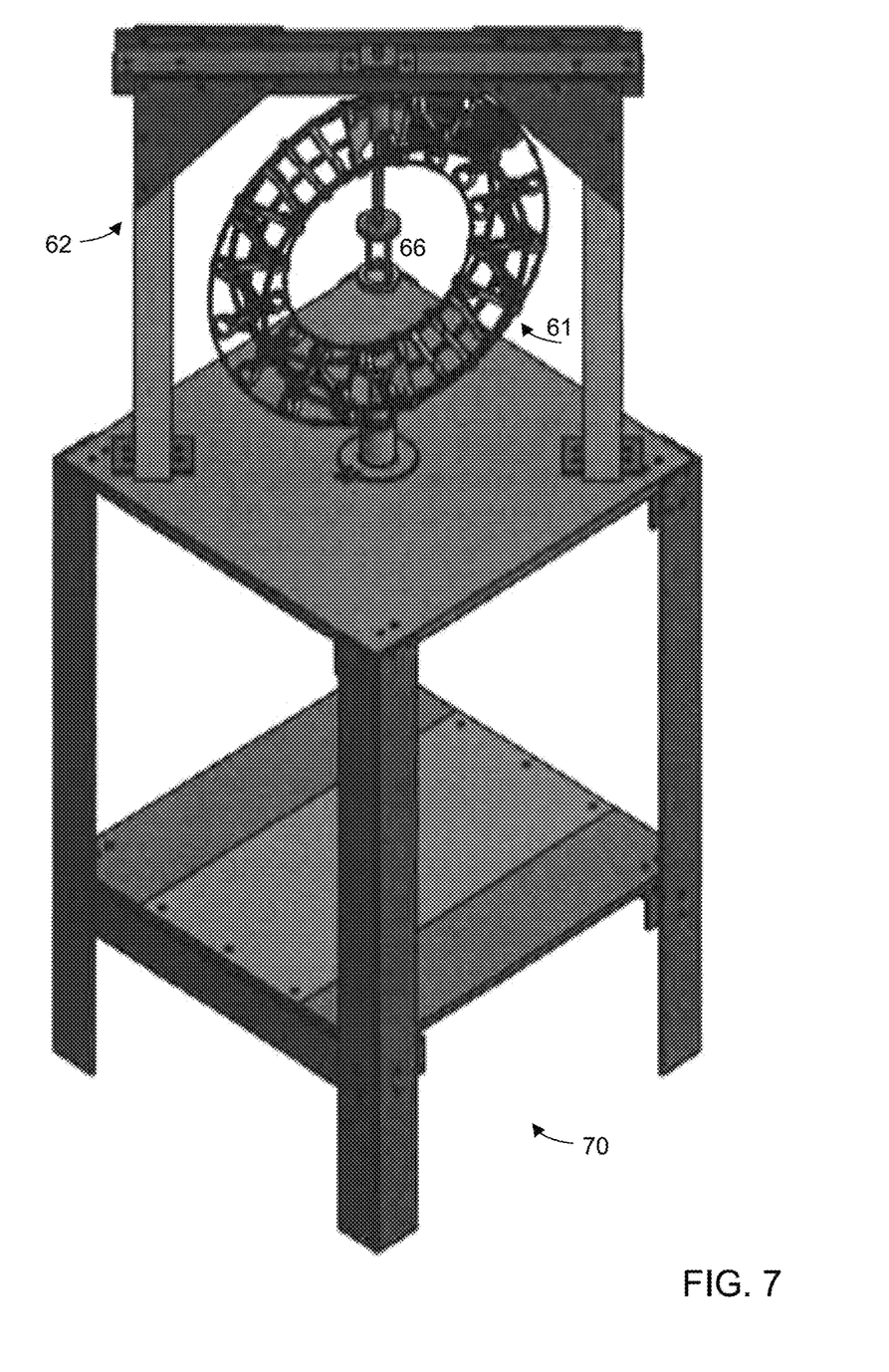
FIG. 7 illustrates an arrangement of a system that includes a rotatable body.

FIG. 7 illustrates an arrangement of system 70 similar to or the same as system 60 in FIGS. 6A-6B, depicted at a different viewing angle. The same components as described regarding FIGS. 6A-6B may be included in FIG. 7. Support structure 62 may be configured to support body 61 in such a way that body 61 is rotatable with respect to support structure 62. System 70 may include a stationary structure 66 in proximity of the center of body 61.

Figure 8:
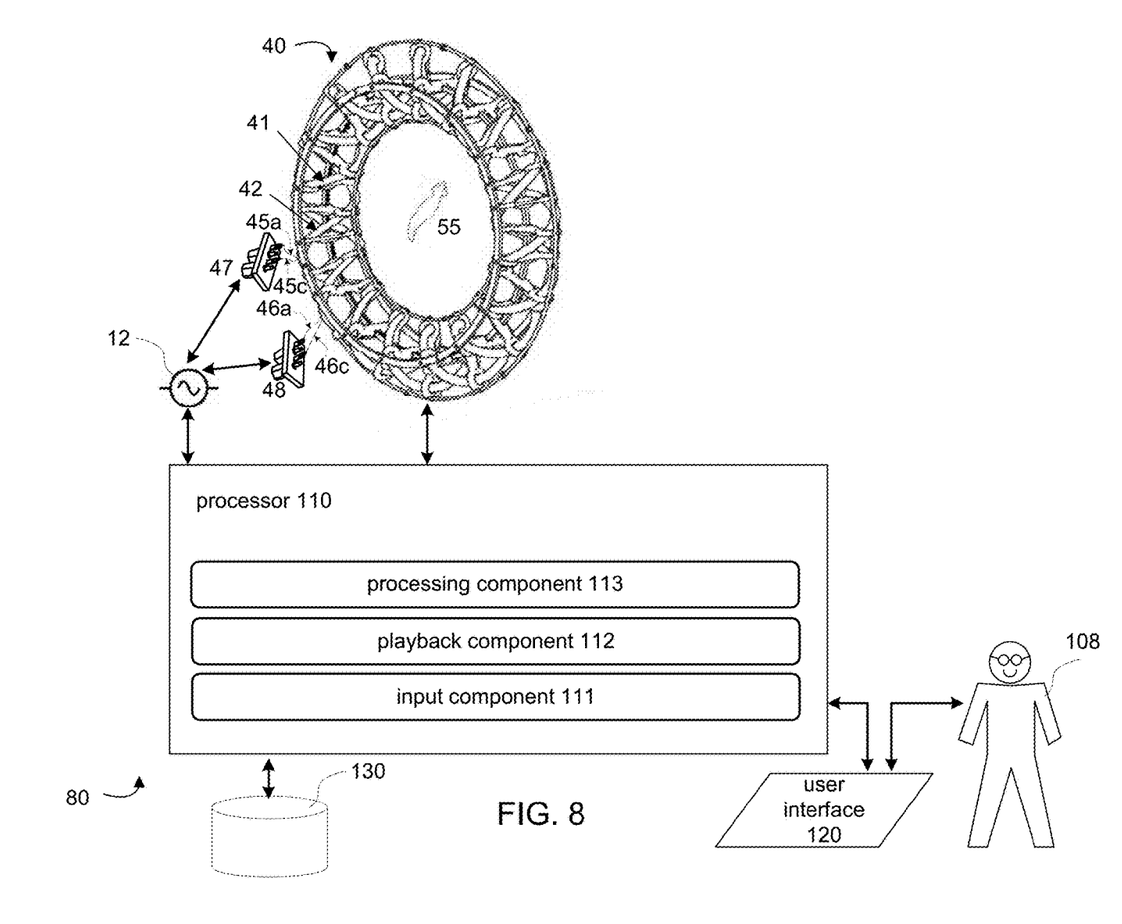
FIG. 8 illustrates a system that includes an exemplary body having two intertwined helically wound runners.

FIG. 8 illustrates an exemplary system 80 that includes one or more of a processor 110, a user interface 120, electronic storage 130, connectors 47 and 48, power source 12, body 40 that includes two intertwined helically wound runners sharing the same circular axis, both runners having conductive wires spirally wound therearound, and/or other components. Body 40 may be similar to body 40 shown in FIG. 4. System 80 may include features and/or components depicted in other figures, including but not limited to FIGS. 4-5-6A-6B-7. For example, body 40 in FIG. 8 may be rotatable. Alternatively, and/or simultaneously, system 80 may include a power source similar to power source 63 in FIG. 6A.

Body 40 may include a first runner 41 and a second runner 42. A first conductive twisted wire may be wound around first runner 41 and electrically coupled to connector 47 via twisted wire ends 45a and 45c. A second conductive twisted wire may be wound around second runner 42 and electrically coupled to connector 48 via twisted wire ends 46a and 46c. Connectors 47 and 48 may be electrically coupled to power source 12 such that one or more electric currents are supplied to the twisted wires wound around first runner 41 and second runner 42, such that an electromagnetic effect (e.g. an electromagnetic field) is created around and/or near body 40. Body 40 may be arranged near organism 55. The depiction of organism 55 as a single element, in this case a planarian, is not meant to be limiting in any way. Though not depicted, system 80 may include a stationary structure or treatment chamber similar to or the same as stationary structure 66 of FIG. 6A. In some implementations, organism 55 may be supported by such a stationary structure, e.g. while body 40 rotates.

Regarding systems and/or bodies 40, 50, 60, 70, and 80, any two intertwined helically wound runners may share the same axis, be congruent, and/or differ by a translation along the axis, e.g. measuring half the pitch.

By way of non-limiting example, additional structures and/or features of any bodies in FIGS. 4-5-6A-6B-7-8 may be described in U.S. Pat. No. 8,653,925, entitled "Double Helix Conductor," which issued Feb. 18, 2014, which is hereby incorporated into this disclosure by reference in its entirety. This patent may also be referred to as "the '925 patent" herein.

The runners in any bodies in FIGS. 4-5-6A-6B-7-8 may be manufactured from one or more of plastic, plastic plated with metals including copper, nickel, iron, soft iron, nickel alloys, fiberoptic materials, and/or other materials (or combinations thereof). In some implementations, one or more runners may be are manufactured from non-conductive material.

The number of turns of a set of twisted wires per inch and/or per helical revolution of a runner may be characteristic measurements/features of an implementation of any of the systems described herein. In some implementations, the number of twists per inch of a twisted wire may be about 2, about 5, about 10, about 20, about 50, about 100, about 150, about 200, about 250, and/or another suitable number of twists. In some implementations, the frequency characteristics of an alternating current and/or the corresponding generated electromagnetic effect or field may be based on, proportional to, and/or otherwise related to the number of twists of a twisted wire. For example, a higher number of twists per inch may correspond to (and/or be used with) a higher operating frequency for the alternating current and/or the corresponding generated electromagnetic effect and/or field. In some implementations, multiple twisted wires (e.g. a first twisted wire wound around a first runner and a second twisted wire wound around a second runner) may have the same direction of twisting, and/or a different direction of twisting. In some implementations, multiple wires (e.g. twisted wires) may be wound around the same runner. In some implementations, a wire may be wound around some or all of one or more struts.

The electric currents supplied to the conductive wires wound around the first and second runner of any bodies in FIGS. 4-5-6A-6B-7-8 may flow in the same direction or the opposite direction. For alternating currents, operating frequencies ranging from more than 0 Hz to about 40 GHz are contemplated. The operating frequencies for the conductive wires wound around the first and second runner of any bodies in FIGS. 4-5-6A-6B-7-8 may be the same or different. Other electrical operating characteristics of the supplied currents, such as phase, amplitude, power-level, and/or other operating characteristics, may be the same or different. Systems using any bodies in FIGS. 4-5-6A-6B-7-8 may be used to exploit the electromagnetic field that is created when electrical power is supplied to one or more wires of one or more bodies.

In some implementations, the conductive wires wound around the first and/or second runner of body 40 are supplied with a first alternating current, e.g. of 216 Hz, and a second alternating current, e.g., of 864 Hz. In some implementations, the currents supplied to body 40 may be 180 degrees out of phase. Supply of the first and second current may create a beat frequency of 432 Hz (corresponds to an "A" note). In some implementations, using a similar approach, beat frequencies of 486 Hz, 512 Hz, 576 Hz, 648 Hz, 729 Hz, 768 Hz, and/or other frequencies may be used, which correspond to "B," "C," "D," "E," "F," and "G" notes, respectively.

In some implementations, the rotational speed of a body, e.g. body 61 in FIG. 6A, may be configured to match, correspond, and/or otherwise be related to one or more frequencies in the one or more alternating currents supplied to the conductive wires wound around the runners of any bodies in FIGS. 4-5-6A-6B-7-8. For example, an alternating current of 216 Hz may be combined with a rotational speed of 216 revolutions per second. In some implementations, the frequency of the alternating current may be a fraction of the rotational speed, and/or vice versa.

Applications for any of the systems described herein may include affecting growth and/or growth rate of plants, livestock, samples, tissue, stem cells, living cells, and/or other (organic) matter, medical applications, therapeutic applications, energy production, energy conversion, energy transformation, adenosine triphosphate (ATP) production, ATP transfer, ATP processing, and/or other applications.

Promotion of growth may include one or more of an increased growth rate, an increased maximum growth level, an increased maximum yield, a shorter duration to reach maturity or regeneration, and an increased feed conversion rate. Using any of the electrical systems described herein, the growth rate, or range of typical growth rates, of the particular type of plant may be increased to a higher growth rate, or higher range of growth rates, for the particular plant. A unit of growth rate may be inch/day, or another unit expressing some length, area, volume, or size per unit of time, and/or another appropriate unit. For some implementations, such as e.g. an implementation using algae or suitable similar plants, growth rate may be expressed though lipid production rate, starch content production rate, biomass content production rate.

For example, a specific type of organism may have a typical maximum growth level, under growing conditions that lack a significant electromagnetic field. Using any of the electrical systems described herein, the maximum growth level, or range of typical maximum growth levels, of the specific type of organism may be increased to a higher maximum growth level, or higher range of maximum growth levels, for the specific organism. Maximum growth level may be expressed in inches, square inches, liters, kilograms, lipid content, and/or another unit expressing some length, area, volume, weight, or size, and/or another appropriate unit.

For example, a particular type of organism may have a typical maximum yield, under growing conditions that lack a significant electromagnetic field. Using any of the electrical systems described herein, the maximum yield, or range of typical maximum yields, of the particular type of organism may be increased to a higher maximum yield, or higher range of maximum yields, for the particular organism. Maximum yield may be expressed in volume or weight per area and/or period, such as kilogram/square feet, or pounds per acre per week, and/or other units as appropriate.

For example, a particular type of organism may have a typical feed conversion (e.g., a rate or ratio), under farming conditions that lack a significant electromagnetic field. Using any of the electrical systems described herein, the maximum feed conversion, or range of typical maximum feed conversions, of the particular type of organism may be increased to a higher maximum feed conversion, or higher range of maximum feed conversions, for the particular organism. In some implementations, feed conversion may be expressed as a percentage of feed that is converted to mass or weight of the organisms, and/or other units as appropriate.

In some implementations, a system including any of the components shown in FIGS. 4-5-6A-6B-7-8 (and/or multiple instances thereof) may be used as a component in an electrical circuit, performing one or more functions and/or applications including a (broadcast) antenna, a (tunable) inductor, a (Tesla) coil, a transformer, a transducer, a transistor, a resistor, a solenoid, a stator for an electrical motor, an electromagnet, an electromagnetic pulse generator, an electromagnetic actuator, an energy conversion device, a position servomechanism, a generator, a stepping motor, a DC motor, a (contact-free) linear drive, an axial flux device, a measurement device for magnetic permeability, a dipole magnet, a device to alter electron and/or particle trajectory, and/or any combination thereof.

Referring to FIG. 8, system 80 may include one or more of user interface 120, one or more physical processors 110, electronic storage 130, one or more power sources and/or current sources (e.g. power source 12a), an input component 111, a playback component 112, a processing component 113, and/or other components.

In some implementations, a system similar to system 80 may include one or more sensors (not shown in FIG. 8). The one or more sensor may be configured to generate output signals conveying information. The information may include electrophysiological information and/or other information. In some implementations, the one or more sensors may include one or more of an audio sensor, a microphone, a stethoscope, a pressure sensor, a motion sensor, a proximity sensor, an electromagnetic sensor, an electrode, a temperature sensor, a current sensor, an optical sensor, an electro-optical sensor, and/or other sensors or combinations thereof. In some implementations, the one or more processors 110 may be configured to provide information-processing capabilities and/or execute computer program components, including but not limited to input component 111, playback component 112, processing component 113, and/or other components. By way of non-limiting example, additional structures and/or features of the one or more sensors, processor 110, user interface 120, electronic storage 130, input component 111, playback component 112, and/or processing component 113, may be described in U.S. patent application Ser. No. 14/194,412, entitled "Health Applications for Using Bio-Feedback to Control an Electromagnetic Field," which was filed Feb. 28, 2014, which is hereby incorporated into this disclosure by reference in its entirety. This application may also be referred to as "the '412 application" herein.

In some implementations, one or more currents supplied to connectors 47 and 48 may correspond to one or more sensor-generated output signals. In some implementations, the one or more currents may correspond to one or more signals generated by a transducer and/or one or more other components of system 80. In some implementations, an alternating current supplied to body 40 may include a carrier signal and a modulating signal. In some implementations, carrier signals used for the alternating current may be radio-frequency signals. As used herein, radio frequency may refer to frequencies between about 30 kHz and about 30 GHz. In some implementations, the modulating signals may have a lower frequency than the carrier signal. For example, the modulating signal may be in the 10-100 MHz range, the 1-10 MHz range, the 100 kHZ-1 MHz range, the 10-100 KHz range, the acoustic range, the telephone range, and/or another suitable range. In some implementations, the modulating signal for the alternating current may be modulated through one or more of amplitude modulation, frequency modulation, phase modulation, digital modulation, and/or other types of modulation. As used herein, the term "acoustic range" may refer to frequencies between about 20 Hz and about 20 kHz. As used herein, the term "telephone range" may refer to frequencies between about 300 Hz and about 3300 Hz.

In some implementations, the one or more frequencies included in an alternating current supplied to body may be based on audio recordings of a note, tone, or chord, generated by a frequency generator and/or a (musical) instrument. For example, a first frequency may be based on the sound of a piano playing an A above middle C (also referred to as A4, which may include sound having a frequency of about 432 Hz, depending on the tuning system used). For example, a second frequency may be based on the sound of some instrument (e.g. a piano) playing a note forming a harmonious interval with A4, which may include sound having a frequency of about 648 Hz. This tuning may be referred to as Pythagorean tuning. Mathematically perfect tuning may combine notes having a 3:2 ratio. Different types of tuning (or tuning systems), including but not limited to equal tempered tuning, may be used and considered within the scope of this disclosure.

Processor 110 may include one or more of a digital processor, an analog processor, a digital circuit designed to process information, a central processing unit, a graphics processing unit, an analog circuit designed to process information, and/or other mechanisms for electronically processing information. Although processor 110 is shown in FIG. 8 as a single entity, this is for illustrative purposes only. In some implementations, processor 110 may include a plurality of processing units.

It should be appreciated that although components 111-113 are illustrated in FIG. 8 as being co-located within a single processing unit, in implementations in which processor 110 includes multiple processing units, one or more of components 111-113 may be located remotely from the other components. The description of the functionality provided by the different components 111-113 described herein is for illustrative purposes, and is not intended to be limiting, as any of components 111-113 may provide more or less functionality than is described. For example, one or more of components 111-113 may be eliminated, and some or all of its functionality may be incorporated, shared, integrated into, and/or otherwise provided by other ones of components 111-113. Note that processor 110 may be configured to execute one or more additional components that may perform some or all of the functionality attributed below to one of components 111-113.

Input component 111 may be configured to obtain information, e.g. from one or more digital audio files, or, alternatively and/or simultaneously, based on sensor-generate output signals. In some implementations, the information may be obtained from storage, e.g. from electronic storage. Information obtained from storage may include electronic audio files in any format, including but not limited to MP3, WMA, WAV, AIFF, and/or other audio formats. In some implementations, information may be obtained from sound sources including frequency generators, phonographs, CD-players, DVD players, AM radio, FM radio, and/or other sound sources.

Processing component 113 may be configured to process the obtained information from input component 111. In some implementations, processing component 113 may be configured to generate a processed signal based on the obtained information from input component 111. For example, processing component 113 may convert, filter, modify, and/or otherwise transform information or signals from input component 111 to generate the processed signal.

Playback component 112 may be configured to produce sound signals based on one or more of the obtained information from input component 111 and/or the processed signal from processing component 113. The sound signals produced by playback component 112 may be coupled electrically to the leads/ends of one or more conductive wires wound around one or more runners of body 40 such that the induced current corresponds to and/or is based on the sound signals. Alternatively, and/or simultaneously, the induced current may be controlled by and/or based on the sound signals produced by playback component 112. In some implementations, the sound signals produced by playback component 112 may be amplified by an amplifier before being electrically coupled to the leads/end of one or more conductive wires. In some preferred implementations, the amplifier may be an audio amplifier ranging between 100 W and 400 W. Other types of amplifiers and/or amplifiers having a different power range are also contemplated.

Electronic storage 130 in FIG. 8 comprises electronic storage media that electronically stores information. The electronic storage media of electronic storage 130 may include one or both of system storage that is provided integrally (i.e., substantially non-removable) with system 80 and/or removable storage that is connectable to system 80 via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 80 to function properly. For example, electronic storage 130 may store sound information and/or electronic audio files (as discussed elsewhere herein), and/or other information. Electronic storage 130 may be a separate component within system 80, or electronic storage 130 may be provided integrally with one or more other components of system 80 (e.g., processor 110).

User interface 120 of system 80 in FIG. 8 is configured to provide an interface between system 80 and a user (e.g., a user 108, a caregiver, a therapy decision-maker, etc.) through which the user can provide information to and receive information from system 80. This enables data, results, and/or instructions and any other communicable items, collectively referred to as "information," to be communicated between the user and system 80. An example of information that may be conveyed to user 108 is an indication of the volume and/or intensity of the sound signals produced by playback component 112. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 by user interface 120 in the form of auditory signals, visual signals, tactile signals, and/or other sensory signals.

It is to be understood that other communication techniques, either hard-wired or wireless, are also contemplated herein as user interface 120. For example, in one implementation, user interface 120 may be integrated with a removable storage interface provided by electronic storage 130. In this example, information is loaded into system 80 from removable storage (e.g., a smart card, a flash drive, a removable disk, etc.) that enables the user(s) to customize system 80. Other exemplary input devices and techniques adapted for use with system 80 as user interface 120 include, but are not limited to, an RS-232 port, RF link, an IR link, modem (telephone, cable, Ethernet, internet or other). In short, any technique for communicating information with system 80 is contemplated as user interface 120.

Figure 9:
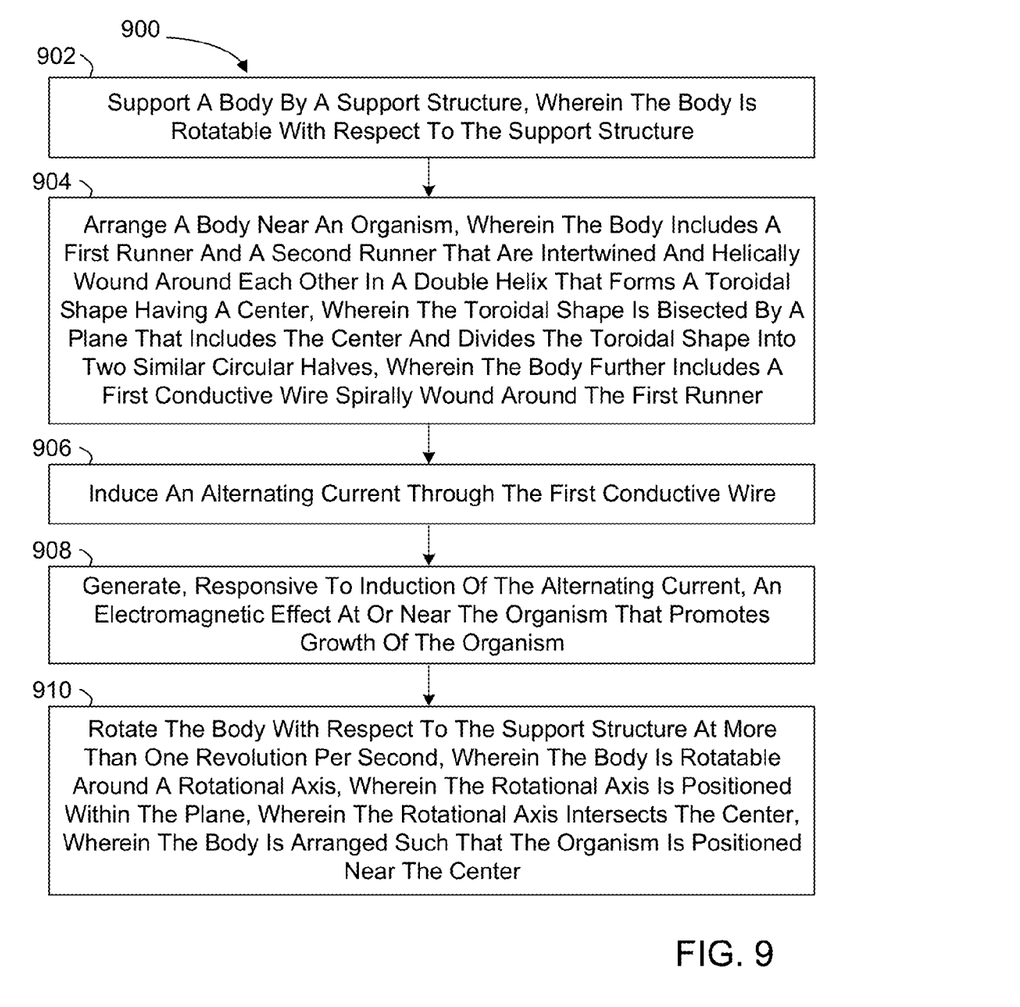
FIG. 9 illustrates a method for providing electromagnetic effects and/or promoting growth of one or more organisms, according to one or more implementations.

FIG. 9 illustrates a method 900 for providing electromagnetic effects. The operations of method 900 presented below are intended to be illustrative. In certain implementations, method 900 may be accomplished with one or more additional operations not described, and/or without one or more of the operations discussed. Additionally, the order in which the operations of method 900 are illustrated in FIG. 9 and described below is not intended to be limiting.

In certain implementations, method 900 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of method 900.

Regarding method 900, at an operation 902, a body is supported by a support structure. The body is rotatable with respect to the support structure. In some embodiments, operation 902 is performed by a support structure the same as or similar to support structure 62 (shown in FIG. 6A and described herein).

At an operation 904, a body is arranged near an organism. The body includes a first runner and a second runner that are intertwined and helically wound around each other in a double helix that forms a toroidal shape having a center. The toroidal shape is bisected by a plane that includes the center and divides the toroidal shape into two similar circular halves. The body further includes a first conductive wire spirally wound around the first runner. In some embodiments, operation 904 is performed by a body the same as or similar to body 61 (shown in FIG. 6A and described herein).

At an operation 906, an alternating current is induced through the first conductive wire. In some embodiments, operation 906 is performed by a power source the same as or similar to power source 12 (shown in FIG. 8 and described herein).

At an operation 908, responsive to induction of the alternating current, an electromagnetic effect is generated at or near the organism that promotes growth of the organism. In some embodiments, operation 908 is performed by a body the same as or similar to body 61 and/or 40 (shown in FIGS. 6A and/or 8 and described herein).

At an operation 910, the body is rotated with respect to the support structure at more than one revolution per second. The body is rotatable around a rotational axis. The rotational axis is positioned within the plane. The rotational axis intersects the center. The body is arranged such that the organism is positioned near the center. In some embodiments, operation 910 is performed by a power source the same as or similar to power source 63 (shown in FIG. 6A and described herein).

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any implementation can be combined with one or more features of any other implementation.

What is claimed is:

1. A system comprising:
  a support structure configured to support a body, wherein the body is rotatable with respect to the support structure; the body comprising:
    a first runner and a second runner that are intertwined and helically wound around each other in a double helix that forms a toroidal shape,
      wherein the toroidal shape comprises a donut shape with a surface and a center, and
      wherein the toroidal shape is bisected by a plane that includes the center and that divides the toroidal shape into two circular halves,
    a plurality of other support structures that support said first runner and said second runner comprising an inner support structure and an outer support structure, wherein said outer support structure comprises a larger radius than said inner support structure, and wherein said inner support structure defines said center,
    one or more rotational elements coupled to said outer support structure, wherein said one or more rotational elements extends beyond said outer support structure and beyond said body at said outer support structure,
    a rotational axis through said one or more rotational elements, wherein said rotational axis intersects said center; and
    a first conductive wire spirally wound around the first runner; and
  one or more power sources that provide an alternating current to the first conductive wire, and provide power to rotate the body around said rotational axis with respect to the support structure at a rotational speed of more than one revolution per second,
  wherein the body rotates at a particular number of revolutions per second,
  wherein the particular number of revolutions corresponds to a frequency of the alternating current,
  wherein the body is rotatable around the rotational axis, wherein the rotational axis is positioned within the plane, wherein the rotational axis intersects the center, wherein the body is configured to be arranged such that an organism is positioned near the center, and
  wherein the system is configured to generate an electromagnetic effect responsive to the alternating current being provided such that the electromagnetic effect promotes growth of the organism.

2. The system of claim 1, wherein the toroidal shape has at least two complete revolutions.

3. The system of claim 1, wherein the first conductive wire is arranged at a fixed distance from the first runner.

4. The system of claim 1, wherein the first conductive wire is a twisted wire.

5. The system of claim 1, wherein the one or more power sources are further configured such that the alternating current has a carrier wave modulated by an acoustic signal, wherein the carrier wave has a higher frequency than the acoustic signal.

6. The system of claim 5, wherein the frequency of the carrier wave is between 1 MHz and 1 GHz.

7. The system of claim 1, wherein the double helix of the body has a diameter between 4 inches and 10 feet.

8. The system of claim 1, wherein said promotion of growth includes one or more of an increased growth rate, an increased maximum growth level, an increased maximum yield, and an increased feed conversion rate.

9. The system of claim 1, further comprising:
one or more physical processors configured via computer-readable instructions to:
obtain information that includes one or more digital audio files;
process the obtained information and generate a processed signal based on the obtained information, and produce sound signals based on the processed signal, wherein the alternating current is dynamically controlled to correspond to the produced sound signals such that one or more of the frequency of the alternating current correspond to one or more frequencies of the produced sound signals.

10. The system of claim 1, further comprising a signal generator configured to generate a signal having a particular frequency, wherein one or both of the alternating current and the power provided to rotate the body are dynamically controlled to correspond to the signal generated by the signal generator.

11. A method for providing electromagnetic effects, the method comprising:
supporting a body by a support structure, wherein the body is rotatable with respect to the support structure;
arranging a body near an organism, wherein the body comprises a first runner and a second runner that are intertwined and helically wound around each other in a double helix that forms a toroidal shape that comprises a donut shape with a surface and a center, and wherein the toroidal shape is bisected by a plane that includes the center and divides the toroidal shape into two circular halves,
wherein the body further comprises
a plurality of other support structures that support said first runner and said second runner comprising an inner support structure and an outer support structure, wherein said outer support structure comprises a larger radius than said inner support structure, and wherein said inner support structure defines said center,
one or more rotational elements coupled to said outer support structure, wherein said one or more rotational elements extends beyond said outer support structure and beyond said body at said outer support structure,
a rotational axis through said one or more rotational elements, wherein said rotational axis intersects said center, and
a first conductive wire spirally wound around the first runner;
inducing an alternating current through the first conductive wire;
generating, responsive to induction of the alternating current, an electromagnetic effect at or near the organism that promotes growth of the organism; and,
rotating the body around said rotational axis with respect to the support structure at a rotational speed of more than one revolution per second,
wherein rotating the body includes rotating the body at a particular number of revolutions per second,
wherein the particular number of revolutions corresponds to a frequency of the alternating current,
wherein the rotational axis is positioned within the plane, and
wherein the body is arranged such that the organism is positioned near the center.

12. The method of claim 11, wherein arranging the body includes forming the toroidal shape that has at least two complete revolutions.

13. The method of claim 11, wherein arranging the body includes winding the first conductive wire at a fixed distance from the first runner.

14. The method of claim 13, wherein winding the first conductive wire includes twisting the first conductive wire into a twisted wire.

15. The method of claim 11, wherein inducing the alternating current is accomplished such that the alternating current comprises a carrier wave modulated by an acoustic signal, wherein the carrier wave comprises a higher frequency than the acoustic signal.

16. The method of claim 15, wherein the frequency of the carrier wave is between 1 MHz and 1 GHz.

17. The method of claim 11, wherein generating the electromagnetic effect effectuates promoting growth of the organism by one or more of an increased growth rate, an increased maximum growth level, an increased maximum yield, and an increased feed conversion rate.

18. The method of claim 11, further comprising:
obtaining information that includes one or more digital audio files;
processing the obtained information and generating a processed signal based on the obtained information, and
producing sound signals based on the processed signal,
wherein inducing the alternating current includes dynamically controlling the alternating current to correspond to the produced sound signals such that one or more of the frequency of the alternating current correspond to one or more frequencies of the produced sound signals.

19. The method of claim 11, further comprising:
generating a signal having a particular frequency,
wherein one or both of the alternating current and power provided to rotate the body are dynamically controlled to correspond to the signal.

20. A system comprising:
a support structure configured to support a body, wherein the body is rotatable with respect to the support structure; the body comprising:
a first runner and a second runner that are intertwined and helically wound around each other in a double helix that forms a toroidal shape,
wherein the toroidal shape comprises a donut shape with a surface and a center, and
wherein the toroidal shape is bisected by a plane that includes the center and that divides the toroidal shape into two circular halves,
a plurality of other support structures that support said first runner and said second runner comprising an inner support structure and an outer support structure, wherein said outer support structure comprises a larger radius than said inner support structure, and wherein said inner support structure defines said center, one or more rotational elements coupled to said outer support structure, wherein said one or more rotational elements extends beyond said outer support structure and beyond said body at said outer support structure, a rotational axis through said one or more rotational elements, wherein said rotational axis intersects said center;

a first conductive wire spirally wound around the first runner; and a second conductive wire spirally wound around the second runner; and one or more power sources that provide one or more alternating currents to the first conductive wire and the second conductive wire, and provide power to rotate the body around said rotational axis with respect to the support structure at a rotational speed of more than one revolution per second, wherein the rotational axis is positioned within the plane, wherein the body is configured to be arranged such that an organism is positioned near the center, wherein the body rotates at a particular number of revolutions per second, wherein the particular number of revolutions corresponds to a frequency of the alternating current, and wherein the system is configured to generate an electromagnetic effect responsive to the one or more alternating currents being provided such that the electromagnetic effect promotes growth of the organism.

* * * * *